United States Patent [19]

Little et al.

[11] Patent Number: 4,822,887

[45] Date of Patent: Apr. 18, 1989

[54] PREPARATION OF DIFLUOROPYRIDINE COMPOUNDS

[75] Inventors: John C. Little, Concord; Charles A. Wilson, Pittsburg, both of Calif.

[73] Assignee: The Dow Chemical Company, Midland, Mich.

[21] Appl. No.: 161,649

[22] Filed: Feb. 29, 1988

Related U.S. Application Data

[63] Continuation of Ser. No. 901,717, Aug. 28, 1986, abandoned, which is a continuation-in-part of Ser. No. 665,588, Oct. 29, 1984, abandoned, which is a continuation-in-part of Ser. No. 564,800, Dec. 23, 1983, abandoned.

[51] Int. Cl.$^4$ ............................................. C07D 213/26
[52] U.S. Cl. .................................................... 546/345
[58] Field of Search ........................................ 546/345

[56] References Cited

U.S. PATENT DOCUMENTS

| 4,031,100 | 6/1977 | Giacobbe | 546/345 |
| 4,071,521 | 1/1978 | Muench | 546/345 |
| 4,480,102 | 10/1984 | Werner | 546/345 |
| 4,565,568 | 1/1986 | Johnston et al. | 71/94 |

FOREIGN PATENT DOCUMENTS 1340421 12/1973 United Kingdom ................ 546/345

OTHER PUBLICATIONS

Finger et al., *J. Organic Chem.*, 28, 1666–1668 (1963).
Chambers et al., *Proc. Chem. Soc.*, 1964, p. 83.
Chambers et al., *J. Chem. Soc.*, 1964, 3573–3576.
Newkome and Paudler, *Contemporary Heterocyclic Chemistry*, pp. 262–264.
Banks et al., *J. Chem. Soc.*, 1865, 594–597.
Abramovitch, *Pyridine and its Derivatives Part 2 Supplement*, pp. 422–423.

*Primary Examiner*—Alan L. Rotman
*Attorney, Agent, or Firm*—Merlin B. Davey; D. Wendell Osborne

[57] ABSTRACT

Alpha, beta-difluoropyridine compounds are prepared by contacting a 2,3-dihalopyridine compound or suitable precursor thereof with an effective amount of KF or CsF in a polar aprotic solvent (diluent) at an elevated temperature under substantially anhydrous conditions with removal of the difluoropyridine products essentially as they are formed. The starting material may optionally be added as the reaction proceeds to minimize decomposition. The reaction is also optionally conducted in the presence of an acid scavenger and/or a crown ether or other phase-transfer catalyst.

8 Claims, No Drawings

PREPARATION OF DIFLUOROPYRIDINE COMPOUNDS

CROSS REFERENCE TO RELATED APPLICATION

This is is a continuation of application Ser. No. 901,717, filed Aug. 28, 1986 now abandoned which application is a continuation-in-part of Ser. No. 665,588 filed Oct. 29, 1984 abandoned which in turn was a continuation-in-part of Ser. No. 564,800 filed Dec. 23, 1983, now abandoned.

BACKGROUND OF THE INVENTION

The present invention relates to the preparation of alpha, beta-difluoropyridine compounds employing potassium fluoride (KF) and/or cesium fluoride (CsF) as the fluorinating agent.

Alkali metal fluorides are well-known agents for the conversion of ring-chlorinated pyridines to the corresponding fluoropyridines. Thus, Finger, et al. (J. Org. Chem. 28, 1666 (1963)), found that KF in dimethyl sulfone at 200° C. over a period of time converted 2-chloropyridine to 2-fluoropyridine. Similarly, 2,3,5-trichloro- and 2,3,5,6-tetrachloropyridine gave the 2-fluoro- and 2,6-difluoro-3,5-dichloropyridines.

It is equally well-known that the exchange of chlorine on pyridine for fluorine using the nucleophilic action of fluoride ion very strongly favors replacement at the alpha- or gamma-positions of chloropyridines, with a beta-chlorine remaining essentially inert. Thus, in addition to the above cases, it has been noted by Chambers, et al. (Proc. Chem. Soc. 1964, 83) that pentachloropyridine, for example, strongly favors exchange at the alpha- and gamma-positions when heated to ca. 200° C. in a polar, aprotic diluent, and only under extreme conditions (anhydrous KF, 400°–500° C., 24 hr) does the exchange of the beta (3- and 5-) chlorines occur. Moreover, whenever this exchange at the beta (3- and/or 5-) position has been observed, it has been limited to fully-substituted chloropyridines: the abovementioned 2,3,5,6-tetrachloropyridine (having a hydrogen at the 4-position) gives only decomposition products under these conditions (Chambers, loc cit.). In closely-related substitution reactions, a betachloropyridine has been found to be 10,000-100,000 times less reactive than the alpha-chloro- or gammachloropyridine, and theoretical explanations have been offered (Newkome and Paudler, "Contemporary Heterocyclic Chemistry", New York, John Wiley (1982), pp 262-3).

European Patent Application No. 63,872 teaches that it is known to react chloropyridines with KF, in the presence or absence of a polar aprotic diluent, in order to replace chlorine by fluorine. This reference discloses on page 5 that when 2,3-dichloro-5-(trichloromethyl)-pyridine is allowed to react with KF the chlorine in the 3-position (betaposition) remains unchanged while all the other chlorine atoms are replaced by fluorine. The resulting product is 3-chloro-2-fluoro-5-(trifluoromethyl)pyridine.

Similarly, the use of CsF as a fluorinating agent is taught in, e.g., European Patent Application Nos. 104,715 and 97,460. These applications teach what are believed to be the first examples of direct substitution (with fluoride ion) of fluorine for the chlorine on a 3-chloropyridine having hydrogen on the ring. EP No. 97,460 cites the reaction of CsF with 3-chloro-2-cyano-5-(trifluoromethyl)pyridine, to yield the beta-fluoropyridine.

In this example, the well-known influence of an adjacent cyano group on an aromatic ring, which powerfully activates a halogen (chlorine) towards substitution (by fluoride), is believed to be operating.

EP No. 104,715 discloses that fluoride ion from cesium fluoride in an aprotic diluent will react with 3-chloro-2-fluoro-5-(trifluoromethyl)p-yridine to give 2,3-difluoro-5-(trifluoromethyl)pyridine.

This reference teaches in a preferred embodiment the use of about 50% molar excess of CsF in dimethyl sulfoxide (DMSO) diluent at 120°–125° for about 48 hours, and the method gives yields of 48–58%.

SUMMARY OF THE INVENTION

In accordance with the present invention, alpha, or beta-difluoropyridines useful as herbicide intermdiates, are by causing 2,3-dihalo-5-chloro- or 5-bromopyridine compounds to react with an effective amount of KF or CsF under substantially anhydrous conditions in a suitable polar aprotic diluent at elevated temperatures while removing the product 2,3-difluoropyridine essentially as it is formed. The starting material is optionally added advantageously at essentially the rate of removal of the product difluoropyridine.

DETAILED DESCRIPTION OF THE INVENTION

In accordance with the present invention, alpha, beta-difluoropyridines are prepared by a process which comprises causing an alpha, beta-dihalopyridine where "halo" represents chloro or bromo to react with potassium fluoride or cesium fluoride under substantially anhydrous conditions in a suitable polar aprotic diluent at elevated temperatures, while removing the product 2,3-difluoropyridine by distillation essentially as it is formed.

In a variant of this invention, the alpha-beta-dihalopyridine starting material may optionally be generated in situ by starting with an alpha, beta-dihalopyridine (where "halo" again represents chloro or bromo, and taking advantage of the previously-mentioned, well-known tendency of alpha-halopyridines to exchange with fluoride ion. Under the reaction conditions, use of additional fluoride (KF or CsF) allows the generation of the required alpha-fluoro-beta-dihalopyridine, which is then converted to the desired product alpha, beta-difluoropyridine.

Of particular interest in this variant form are the conversions of 2,3,5-trichloropyridine and 2,3,5-tribromopyridine to 2,3-difluoro-5-chloropyridine and 2,3-difluoro-5-bromopyridine, respectively. The latter two compounds are useful as chemical intermediates in the preparation of 2-(4-((5-chloro (or bromo)-3-fluoro) pyridinyl-2-oxy)phenoxy propionic acid and agriculturally acceptable derivatives thereof, i.e., for example, salts, esters and amides, which are known herbicidal agents as taught in EPO patent application No. 83,556.

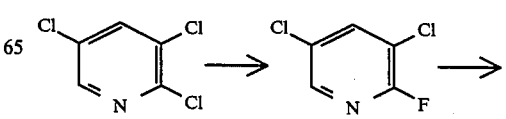

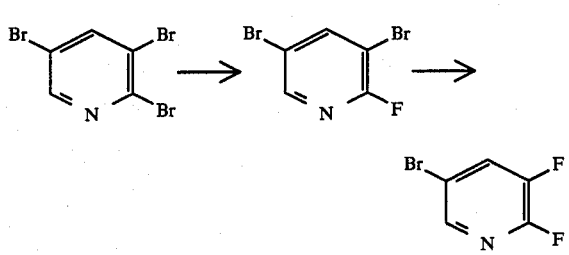

In the process of this invention, the starting material is often advantageously added at essentially the rate of removal of the product 2,3-difluoropyridine thus helping to minimize contact of both the starting material and the product with the reaction medium, in which they tend to decompose.

KF and CsF are the fluorinating agents employed in the present reaction and are commercially available compounds. Substantially anhydrous and finely-divided KF or CsF are preferred. Amorphous or spray-dried forms are particularly preferred. Substantially anhydrous KF and CsF can be prepared, for example, by drying in vacuo at 140°–250° C. for several hours.

Polar aprotic diluents are employed as the reaction medium in the present process. Suitable polar aprotic diluents include dimethylsulfoxide (DMSO), dimethylformamide (DMF), dimethylacetamide, diethylacetamide, methyl isobutyl ketone, hexamethylphosphoric acid triamide, tetramethylurea, sulfolane (tetramethylenesulfone), and N-methylpyrrolidinone (NMP). Preferred diluents include NMP, DMSO and sulfolane.

Optionally, the reaction may be conducted in the presence of
 (a) an acid scavenger, such as, an alkali metal carbonate, and/or in the case of employing KF as the fluorinating agent,
 (b) a phase-transfer catalyst.

The present reaction is conducted under substantially anhydrous conditions at elevated temperatures of from about 50° C. up to the boiling point of the solvent. Preferred temperat-ure ranges are from about 100° C. to 200° C. when CsF is used, and from 150° C. up to the boiling point of the solvent when KF is used.

Pressures of from about 10 mm Hg to 10 atm may also be employed, with preferred pressures of about 50 mm Hg to 1 atm.

A fractional distillation system having 1 to 100 theoretical plates is conveniently employed to separate the product from the starting material. A preferred system has 5 to 20 theoretical plates.

The optimum combination of temperature and pressure is actually a function of the particular system being studied and can be determined by routine experimentation. In general the pressure is chosen so as to provide convenient separation of the desired product from the starting material through the fractional distillation system while allowing a reaction temperature (distillation pot temperature) high enough to maintain a satisfactory reaction rate. Experimental determination of the reaction rate can be conveniently judged by observing the drop in the observed reflux temperature in the distillation column from that of the starting material to that of the product.

Substantially anhydrous reaction conditions are preferred; these may be achieved employing standard drying techniques. For example a typical glass laboratory reactor can be dried by distilling the polar aprotic solvent nder a vacuum before addition of the reactants. Optionally, a small amount (5–10 percent by weight of the polar aprotic solvent) of a non-polar solvent such as an aromatic hydrocarbon (toluene, xylene, etc.) may be added to the polar aprotic solvent to aid in the removal of water by azeotropic distillation. Residual water in the reactor system is also often removed by azeotropic distillation.

The amount of polar aprotic solvent is not critical but it is advantageous to employ enough solvent to keep the starting material in solution at reaction temperatures, generally about 2 to about 25 parts by weight solvent per part by weight pyridine starting material. The relative proportions of reactants to be employed are not critical because some of the product will be formed when employing any proportion of reactants. The reaction consumes the reactants, however, in the ratio of one mole of fluorinating agent per mole of exchangeable halogen atoms present in the starting material. Usually from about 0.75 to about 1.5 moles of KF or CsF are employed per mole of exchangeable halogen in the pyridine starting material.

In carrying out the present reaction, neither the rate nor the order of addition of the reactants is critical. Usually, the solvent and fluorinating agent are added to an appropriate reaction vessel and the reaction is dried by distilling a small portion of the solvent. The starting material or precursor compound is then added to the reaction vessel which is thereafter followed by heating of the reaction mixture at a suitable pressure, usually 50 mm Hg to 1 atm, to provide convenient separation of the desired product as it is formed. In an especially preferred mode, the starting material is added to the fluorinating agent (KF or CsF) in the solvent under the optimized reaction conditions at about the same molar rate as the formation and removal of the product. If an acid scavenger, a nonpolar solvent, or catalyst is employed in the reaction, then they are advantageously added to the solvent/fluorinating agent mixture prior to drying the reactor vessel.

The present reaction is typically conducted in the presence of agitation sufficient to maintain an essentially uniform dispersion of the reactants in the solvent.

Usually the reaction using KF without a catalyst is complete in 16 to 24 hours. Catalysts are optionally employed, when KF is used, to increase the reaction rate. When a catalyst is used with KF, 8 to 16 hours are usually required. When CsF is used, 2 to 8 hours are normally sufficient. Suitable catalysts include phase-transfer catalysts. The catalyst is added to the present reaction mixture in an amount of from about 0.0001 to about 0.1 mole per mole of pyridine starting material, advantageously from about 0.001 to about 0.075 molar equivalents and preferably from about 0.01 to about 0.05 molar equivalents.

Phase-transfer catalysts are well known compounds and include (a) quaternary ammonium or phosphonium salts containing 10 or more carbon atoms and (b) macrocyclic polyethers commonly known as crown ethers. Suitable crown ether catalysts include 18-crown-6;

dicyclohexano-18-crown-6; dibenzo-18-crown-6; 15-crown-5. A related species, tris(3,6-dioxaheptyl)amine is also efficaceous. Suitable quaternary ammonium and phosphonium salts include tetra-n-alkylammonium salts and tetra-n-alkylphosphonium. salts. Particular catalysts include benzyltriethylammonium chloride, methyl trioctylammonium chloride, tetra-n-butylammonium chloride, tetra-n-butylammonium hydrogen sulfate, tetra-n-butylphosphonium chloride and cetyl trimethylammonium bromide. The anion of the phosphonium and ammonium salts of $F^\theta$ or any anion which readily converts to $F^\theta$, such as for example, $Cl^\theta$, $Br^\theta$, $I^\theta$, $OH^\theta$, $OAc^\theta$, etc. Preferred catalysts include 18-crown-6 and cetyltrimethylammonium bromide.

Acid scavengers are optionally employed in the present reaction to consume or inactivate traces of HCl or HF which may be present or generated during the reaction. Suitable acid scavengers include alkali metal carbonates such as anhydrous $K_2CO_3$ and anhydrous $NaCO_3$. A preferred acid scavenger is anhydrous $K_2CO_3$. The acid scavengers are added to the present reaction mixture in an amount of from about 0.001 to about 0.1 mole per mole of pyridine starting material. Preferably, from about 0.03 to about 0.05 molar equivalents are employed.

The solvent used in the process of this invention may be distilled to recover it free from impurities and re-used. Alternatively, it has been found that, under certain conditions, the solvent may be re-used without distillation by simply filtering or decanting from the spent potassium or cesium salts and charging fresh KF or CsF. Solvents such as NMP have been re-used as many as 4 times in this manner before further purification was necessary, and additional recycles may be possible.

The following examples illustrate the practice of the present invention and should not be construed as limiting. No attempt has been made to balance any chemical equations described herein. All temperatures are in °C. and boiling points are at atmospheric pressure unless otherwise stated.

EXAMPLE 1

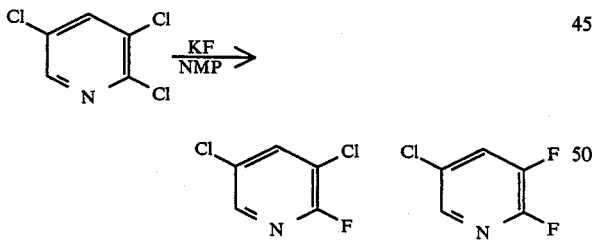

A 5-liter flask equipped with an efficient tirrer, thermometer, temperature controller, 250 watt infared heat lamp, a reduced pressure control device and a 1 inch Od 1.5/tray glass Oldershaw (sieve plate) distillation column having a vapor fraction cutter, condenser and a water-jacketted receiver was charged with 3,500 ml of NMP, 290 g (5.0 moles) of powdered KF which had been dried at 140° C. in vacuo. A total of 80 ml of distillate (NMP and water) was removed (b.p. 140°-142° C./170 mm) and then 376 g (2.06 moles) of 2,3,5-trichloropyridine was added. The mixture was stirred vigorously at 140° C. for 17 hours, and then the temperature was increased to 190° C. under a nitrogen atmosphere for the next 16 hours. The reaction mixture was cooled and subjected to vacuum distillation to remove 135 g of liquid, b.p. 86°-126° C./150 mm, which contained, by glpc analysis, 45 g, 33% of 5-chloro-2,3-difluoropyridine and 86 g, 64% of 3,5-dichloro-2-fluoropyridine.

The reaction mixture was again heated to 190° C. with good stirring for 20 hours, cooled and subjected again to vacuum distillation to yield 198 g of liquid, b.p. 100°-127° C./100 mm, which was found by glpc analysis to contain 15% of 5-chloro-2,3-fluoropyridine and 71% of 3,5-dichloro-2-fluoropyridine. The total net yield, therefore, of 5-chloro-2,3-difluoropyridine was 74.1 g, 24% with a 227.5 g, 67% yield of the intermediate, 3,5-dichloro-2-fluoropyridine being available for recycle. There was 91% recovery of product and by-product.

A purified sample of 5-chloro-2,3-difluoropyridine was found to have a b.p. of 135°-136° C. (1 atm.). 3,5-Dichloro-2-fluoropyridine was found to have a b.p. of 173°-174° C. (1 atm.). Both compounds had proton and fluorine NMR spectra consistent with their assigned structures.

EXAMPLE 2

To a 1 liter 3-necked flask equipped as described in Example 1 was charged 600 ml of DMSO, and 20 ml of solvent was distilled (b.p. 140°-142°/150 mm) to dry the system. The vacuum was released and there was added 224 g (1.47g-mol) of CsF which had been dried in vacuo at 250° C. for 16 hours and then pulverized, followed by 3 g of potassium carbonate and 104 g (0.57 g-mol) of 2,3,5-trichloropyridine. The mixture was heated to reflux at 200 mm pressure for 2 hours, during which time the head temperature was observed to drop from 122° to 100° C. The pressure was then reduced from 177 mm, and slow distillation over the next 7 hours while the pot temperature was being raised from 133° C. to 142° C. gave a total of 60.2 g of material, b.p. 96°-108° C./175 mm. Glpc analysis indicated the presence of 45.6 g of 5-chloro-2,3-difluoropyridine and 7.9 g of 3,5-dichloro-2-fluoropyridine. Redistillation yielded 43 g of the former as a colorless oil, b.p. 83°-84° C./150 mm and 7.9 g of a semisolid fraction, b.p. 122°-123° C./150 mm, which was determined by glpc analysis to be 93.5 percent pure 3,5-dichloro-2-fluoropyridine. The proton and fluorine NMR spectra were consistent with the assigned structures.

EXAMPLE 3

To a 1 liter 3-necked flask equipped as described in Example 1 was charged 600 ml of DMSO, and the material was heated to distill ca. 15 ml of solvent to dry the system (b.p. 140° C./200 mm). The vacuum was released and 186 g (1.22 g-mol) CsF (dried 16 hours at 200° C. in vacuo), 3 g of potassium carbonate and 133 g (0.80 g-mol) of 3,5-dichloro-2-fluoropyridine was added. The mixture was heated to reflux at 200 mm; the head temperature dropped from an initial 126° C. to 97° C./200 mm over 30 minutes, and distillation was then carried out over 5.25 hours at 97°-106° C./200 mm, pot temperature 139°-144° C., to yield 68.8 g of material. Distillation was interrupted at this point and the reaction was shut down overnight. Continuation the next day yielded an additional 21.7 g of material, b.p. 96°-118° C./200 mm over 3 more hours while the pot temperature was raised from 142° C. to 145° C. Analysis of the product showed the presence of a total of 74.8 g of 5-chloro-2,3-difluoropyridine and 10.1 g of the starting material, for a yield of 67 percent at 92 percent conversion. Redistillation gave a recovery of 74 g of 5-chloro-2,3-difluoropyridine, b.p. 84°–86° /150 mm (135°–136° C./1 atm.) which was 99.1 percent pure by glpc analysis.

EXAMPLE 4

To a 1 liter flask equipped as described in Example 1 was charged 19 g (0.31 mole) of dried KF and 300 l of sulfolane. A small amount of the solvent was distilled in vacuo to dry the system and then 50 g (0.16 mole) of 2,3,5-tribromopyridine was added. The mixture was heated with stirring to 210° for 3.5 hours. and then vacuum (190 mm) was applied to bring the system to reflux. Ca. 4 g of liquid, b.p. 90°–140°/190mm was removed, and then 9 g (0.15 mole) of additional dried KF was charged. Over the next 18 hours an additional 5 g of material was distilled, b.p. 110°–160°/190 mm, with the pot temperatue rising to 225° C. Analysis of the combined products by glpc showed the presence of ca. 3.3 g of 5-bromo-2,3-difluoropyridine and 1.4 g of 5-bromo-2-fluoropyridine, plus a smaller amount of material tentatively identified as 2,3,5-trifluoropyridine. Analysis of the material remaining in the reaction flask showed the presence of 13.6 g of 3,5-dibromo-2-fluoropyridine.

A purified sample of 5-bromo-2,3-difluoropyridine had b.p. ca. 164° and the $^1$H and $^{19}$F NMR spectra were consistent with the assigned structure. A sample of 5-bromo-2-fluoropyridine had b.p. 175° and the NMR spectra were likewise consistent with the assigned structure.

EXAMPLE 5

To a 1 liter 3-necked flask equipped with a simple distillation head, thermometer, stirrer and heater was charged 72 g (0.47 mole) of dried CsF, 2.5 g of $K_2CO_3$ and 400 ml of sulfolane. Ca. 20 ml of the solvent was distilled in vacuo to dry the ystem, and 50 (0.16 mole) of 2,3,5-tribromopyridine was added. The mixture was heated to 180°–190° C. for 7 hr. Vacuum distillation yielded a mixture which, by glpc analysis, showed the presence of a 45% of yield of 2,3-difluoro-5-bromopyridine, and small amounts of 2-fluoro-5-bromopyridine and 2,3,5-trifluoropyridine. Analysis of the residual material in the sulfolane showed the presence of 3,5-dibromo-2-fluoropyridine.

What is claimed is:
1. A method of preparing a product compound having the formula

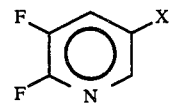

wherein X is Br or Cl, which comprises contacting a starting compound having the formula

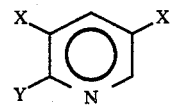

wherein each X is individually Br or Cl and Y is F, Cl or Br with an effective amount of KF in a polar aprotic diluent at an effective temperature of from 50° C. to the boiling point of the diluent, optionally in the presence of a phase-transfer catalyst, removing the product compound by distillation essentially as it is formed, and, optionally, adding additional starting compound as the product compound is removed.

2. Method of claim 1 wherein the 2,3-dihalopyridine compound is 2,3,5-trichloropyridine and the product is 2,3-difluoro-5-chloropyridine.

3. Method of claim 1 wherein the 2,3-dihalopyridine compound is 2,3,5-tribromopyridine and the product is 2,3-difluoro-5-bromopyridine.

4. Method of claim 1 wherein the fluoride salt is KF and the reaction is carried out in the presence of (a) a phase-transfer catalyst and optionally (b) an acid scavenger.

5. Method of claim 1 wherein the diluent is dimethylsulfoxide, sulfolane or N-methylpyrrolidinone.

6. Method of claim 1 wherein the salt is KF and the reaction temperature is from 175° C. up to the boiling point of the diluent.

7. Method of claim 1 wherein the reaction is carried out at a pressure from 50 to 300 mm Hg.

8. Method of claim 4 wherein the phase-transfer catalyst is a quaternary ammonium halide, a crown ether, or tris(3,6-dioxaheptyl)amine.

* * * * *

UNITED STATES PATENT AND TRADEMARK OFFICE
CERTIFICATE OF CORRECTION

PATENT NO. : 4,822,887

DATED : April 18, 1989

INVENTOR(S) : John C. Little, Charles A. Wilson

It is certified that error appears in the above-identified patent and that said Letters Patent is hereby corrected as shown below:

On the title sheet, in "OTHER PUBLICATIONS", after "Banks et al., *J. Chem. Soc.*," delete "1865" and insert -- 1965 --;

Col. 1, line 7, delete the second "is";

Col. 2, line 9, delete ")p-yridine" and insert -- )pyridine --;

Col. 2, line 18, "intermediates" has been misspelled;

Col. 2, line 19, after "are" insert -- prepared --;

Col. 2, line 48, delete "-dihalopyri-" and insert -- -halopyri- --;

Col. 3, line 49, "temperature" has been misspelled;

Col. 4, line 8, "under" has been misspelled;

Col. 5, line 5, after "-alkylphosphonium" delete ".";

Col. 5, line 55, "stirrer" has been misspelled;

Col. 5, line 56, "infrared" has been misspelled;

Col. 7, line 10, delete "300 l" and insert -- 300 ml --;

Col. 7, line 14, after "hours" delete ".";

Col. 7, line 20, "temperature" has been misspelled;

UNITED STATES PATENT AND TRADEMARK OFFICE
CERTIFICATE OF CORRECTION

PATENT NO. : 4,822,887

DATED : April 18, 1989

INVENTOR(S) : John C. Little, Charles A. Wilson

It is certified that error appears in the above-identified patent and that said Letters Patent is hereby corrected as shown below:

Col. 7, line 40, "system" has been misspelled;

Col. 7, line 44, before "yield" delete "of";

Col. 8, line 31, "Method" has been misspelled.

Signed and Sealed this

Eleventh Day of February, 1992

Attest:

HARRY F. MANBECK, JR.

*Attesting Officer*  *Commissioner of Patents and Trademarks*